United States Patent [19]

Haber et al.

[11] Patent Number: 5,104,378

[45] Date of Patent: Apr. 14, 1992

[54] SYRINGE HAVING MEANS FOR RETRACTING, CANTING AND DESTROYING A NEEDLE CANNULA

[75] Inventors: Terry M. Haber, El Toro; William H. Smedley, Lake Elsinore; Clark B. Foster, Laguna Niguel, all of Calif.

[73] Assignee: Habley Medical Technology Corporation, Laguna Hills, Calif.

[21] Appl. No.: 421,258

[22] Filed: Oct. 13, 1989

[51] Int. Cl.[5] .......................... A61M 5/00; A61M 5/32
[52] U.S. Cl. ..................................... 604/110; 604/195
[58] Field of Search ........ 604/110, 111, 187, 194–197, 604/218, 220, 228

[56] References Cited

U.S. PATENT DOCUMENTS

| | | | |
|---|---|---|---|
| 2,722,215 | 11/1955 | Dahlgren | 604/157 |
| 3,306,290 | 2/1967 | Weltman | 604/197 |
| 3,320,954 | 5/1967 | Cowley | 604/110 |
| 3,796,359 | 3/1974 | Dick | 604/197 |
| 3,811,441 | 5/1974 | Sarnoff | 604/218 |
| 4,026,287 | 5/1977 | Haller | 604/195 |
| 4,507,117 | 3/1985 | Vining et al. | 604/196 |
| 4,542,749 | 9/1985 | Caselgrandi et al. | 604/196 |
| 4,553,962 | 11/1985 | Brenet | 604/198 |
| 4,562,844 | 1/1986 | Carpenter et al. | 604/220 |
| 4,592,744 | 6/1986 | Jagger et al. | 604/197 |
| 4,643,199 | 2/1987 | Jennings, Jr. et al. | 604/110 |
| 4,650,468 | 3/1987 | Jennings, Jr. | 604/194 |
| 4,692,156 | 9/1987 | Haller | 604/195 |
| 4,770,655 | 9/1988 | Haber et al. | 604/110 |
| 4,804,370 | 2/1989 | Haber et al. | 604/195 |
| 4,808,169 | 2/1989 | Haber et al. | 604/195 |
| 4,813,936 | 3/1989 | Schroeder | 604/195 |
| 4,826,484 | 5/1989 | Haber et al. | 604/110 |
| 4,838,870 | 6/1989 | Haber et al. | 604/187 |
| 4,874,382 | 10/1989 | Lindemann et al. | 604/195 |

*Primary Examiner*—C. Fred Rosenbaum
*Assistant Examiner*—Sharon Rose
*Attorney, Agent, or Firm*—Hawes & Fischer

[57] ABSTRACT

A cost effective, disposable, safety syringe having a conventional single ended hypodermic needle cannula retained in an axially extended position at the distall end of a cylinder by an epoxy bond formed with the central core of a needle carrying hub. A locking and retracting probe extends proximally into the syringe cylinder from the central core of the needle hub. A piston assembly, having an offset locking bore formed therein, is advanced distally through the cylinder to expulse fluid therefrom via the cannula and to receive the locking and retracting probe within the locking bore. A continued distal advancement of the piston assembly through the cylinder causes the central core and the cannula supported thereby to be broken away from the needle hub. Therefore, when the piston assembly is withdrawn proximally through the cylinder, the cannula is correspondingly retracted within and shielded by the cylinder to avoid an accidental needle stick and the spread of disease. The cannula is canted within the cylinder, such that another distal advancement of the piston assembly through the cylinder causes the cannula to be axially collapsed and, thereby, destroyed against a relatively thick shield formed at the distal aspect of the syringe cylinder.

18 Claims, 4 Drawing Sheets

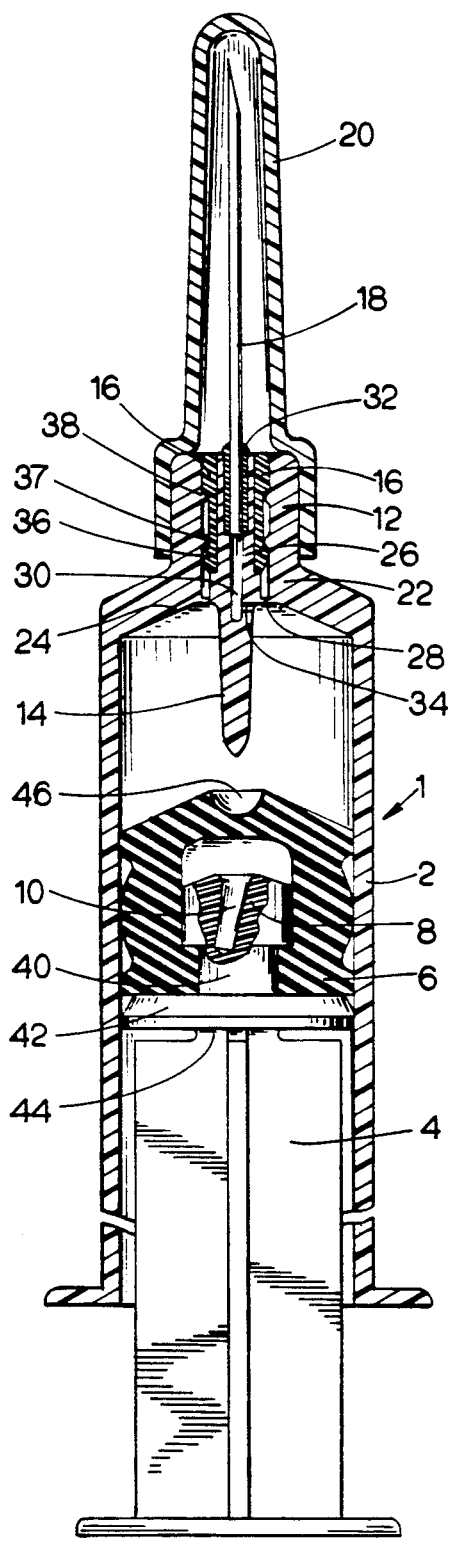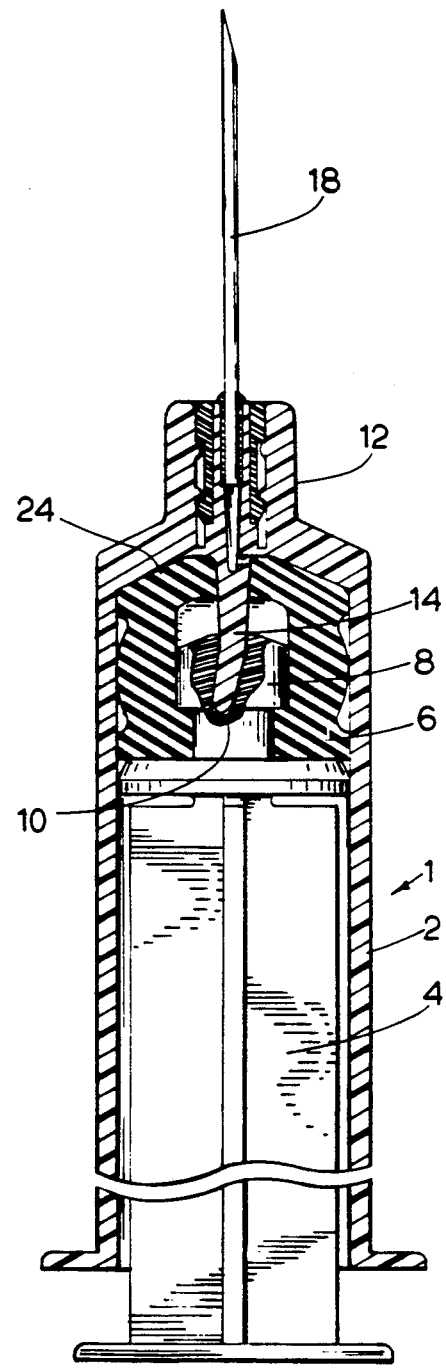
FIG. 3
FIG. 4

SYRINGE HAVING MEANS FOR RETRACTING, CANTING AND DESTROYING A NEEDLE CANNULA

BACKGROUND OF THE INVENTION

1. FIELD OF THE INVENTION

This invention relates to a cost effective, disposable, safety syringe having a conventional single ended hypodermic needle cannula bonded to and extending axially from a needle hub at the distal end of the syringe cylinder and, more particularly, to means for engaging, retracting, canting and destroying said cannula within the cylinder to form a compact package suitable for handling and disposal while avoiding an accidental needle stick and the possible spread of disease.

2. BACKGROUND ART

Hypodermic syringes are used for a variety of injection procedures including the delivery of medicinal drops to a recipient. However, once the injection procedure is completed and the syringe cylinder emptied, problems may arise as a consequence of failing to properly and adequately dispose of the syringe. By way of example, the syringe may be used to treat a patient having a communicable disease. To prevent reuse, the hypodermic needle cannula is sometimes broken before the syringe is discarded. Health care workers are susceptible to accidental and potential infectious needle sticks due to the careless handling of the needle cannula or disposing of the syringe after use. The resulting mini-accidents caused by an accidental needle stick typically require a blood test for such diseases as AIDS and hepatitis. The corresponding cost and inefficiency of testing health care workers who have received an inadvertent needle stick result in considerable waste, which may be particularly damaging to a health care facility striving for economy and efficiency.

Disposable safety syringes are known in the art which include means by which to withdraw a needle cannula from an axially extended position, at which to administer an injection, to a retracted position shielded within the syringe cylinder. However, such safety syringes are typically characterized by unconventional parts and, therefore, a high cost. By way of example, the use of special cannula designs and complex cannula retaining means increase the cost of manufacture and adversely impact the cost effectiveness of the syringe.

It would be more desirable to combine a conventional needle cannula and know manufacturing techniques with the advantages of a retractable cannula to achieve a cost effective safety syringe.

The following United States patents and applications, which have been or will be assigned to the assignee of the present patent application, disclose a safety syringe having a retractable needle cannula that is releasably retained in an axially extended position between a pair of spring-like jaws:

U.S. Pat. No. 4,909,794 issued Mar. 20, 1990
U.S. Pat. No. 4,908,022 issued Mar. 13, 1990
U.S. Pat. No. 4,944,723 issued July 31, 1990
U.S. Pat. No. 4,808,169 issued Feb. 28, 1989; and
U.S. Pat. No. 4,826,489 issued May 2, 1989.

SUMMARY OF THE INVENTION

In general terms, this invention relates to a disposable safety syringe that uses a conventional single ended hypodermic needle cannula and known cannula bonding technology to improve the cost effectiveness of said syringe. The syringe includes a needle hub located at the distal end of the syringe cylinder for supporting the cannula in an axially extended position at which an injection is administered. The needle hub comprises the concentric arrangement of an outer sleeve and an inner central core having a longitudinal channel formed therein. The cannula is received within and bonded (e.g. by means by epoxy, or the like) to the channel formed in the central core of the needle hub. Releasably retained between the outer sleeve and central core of the needle hub is a pair of spring-like jaws which surround said central core and provide a clamping force to an axial support for the cannula. The outer sleeve and inner central core of the hub are connected to one another by a relatively thin, breakaway sealing web. A fluid port extends through the central core of the needle hub to establish a fluid path through which fluid from the syringe cylinder is expulsed via the cannula. A coextensive locking and retraction probe extends proximally from the central core into the cylinder.

A piston assembly, including a piston stem and a hollow elastomeric gasket, moves axially and reciprocally through the syringe cylinder. The gasket is attached to the piston stem at a piston head which includes an offset locking bore that is angled relative to the longitudinal axis of the syringe.

In operation, the piston assembly is advanced distally through the syringe cylinder to expulse the fluid contents thereof until the locking and retraction probe which extends proximally from the central core of the needle hub pierces the gasket for receipt within the locking bore of the piston head. Because of the angled configuration of the locking bore, the proximal tip of the locking and retraction probe is deflected by and locked within said bore, whereby the piston assembly is fixedly connected to the central core. The continued distal advancement of the piston assembly through the cylinder causes the breakaway sealing web to fracture between the outer sleeve and central core of the needle hub, such that the central core is displaced relative to the outer sleeve, and the spring-like jaws are relocated outwardly of said outer sleeve to release the cannula therefrom. A proximal withdrawal of the piston assembly through the cylinder causes a corresponding retraction of the needle cannula into said cylinder by way of the connection of the locking and retraction probe to the locking bore of the piston head. Accordingly, the cannula is surrounded and shielded by the cylinder to prevent an accidental needle stick and the possible spread of a contagious disease.

Because of the angled configuration of the locking bore, the needle cannula is canted within the cylinder to prevent a return of the cannula to the axially extended position. Hence, another distal advancement of the piston assembly through the cylinder causes the cannula to be axially collapsed and destroyed against a relatively thick shield formed at the distal aspect of the cylinder. The cannula is thereby rendered non-reusable, and the syringe is suitable to be safely handled and discarded.

BRIEF DESCRIPTION OF THE DRAWINGS

FIG. 3 is a partial cross-section of the syringe of FIG. 2;

FIGS. 4–7 are partial cross-sections of the syringe in the post-injection configuration to illustrate the operation of said syringe.

DESCRIPTION OF THE PREFERRED EMBODIMENT

Figures 1, 2:
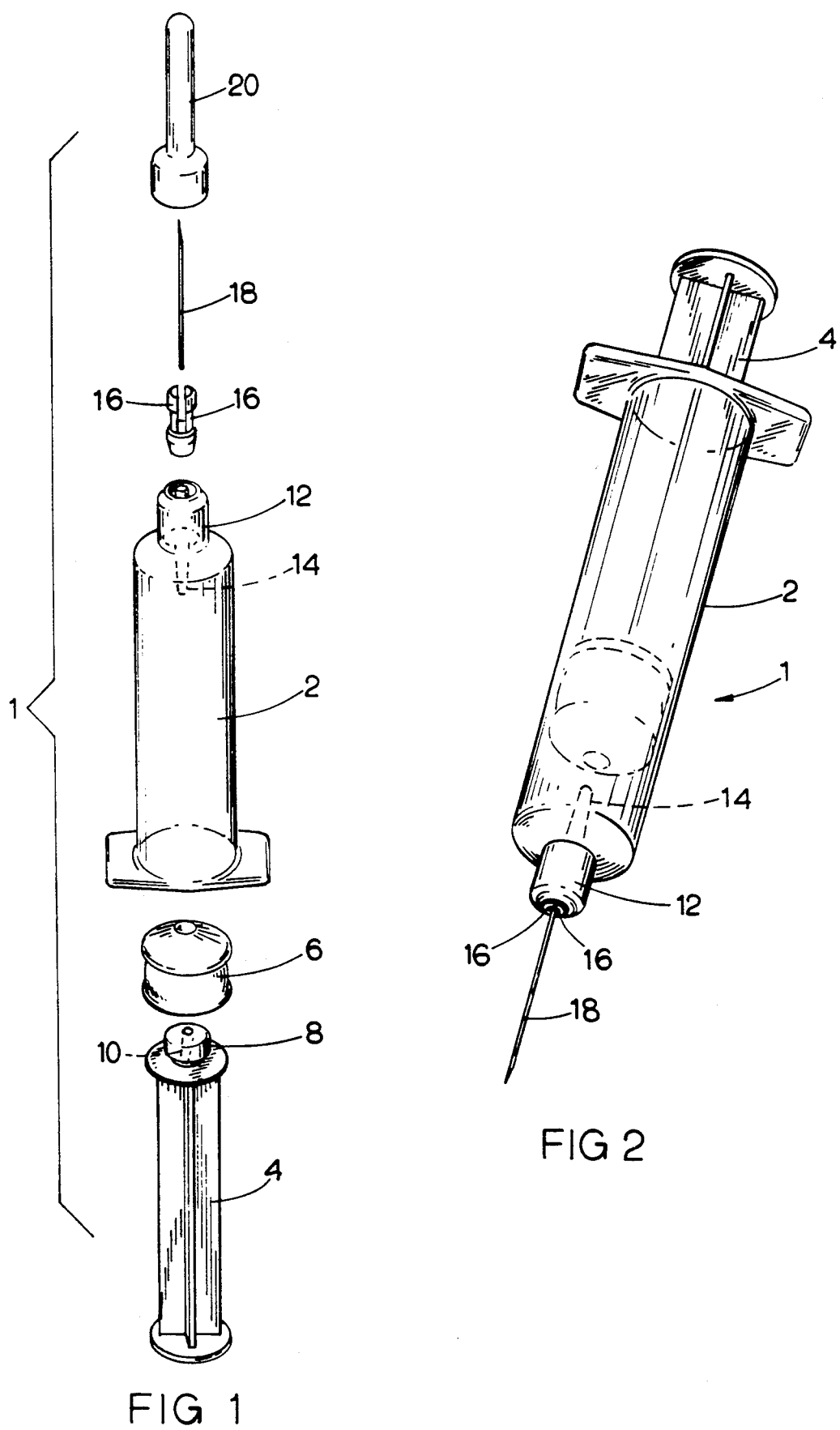
FIG. 1 is an exploded view of the disposable safety syringe according to a first embodiment of the present invention.
FIG. 2 shows the syringe of FIG. 1 in the assembled as-packaged configuration.

The cost efficient, disposable, safety syringe 1 which forms the present invention is best described while referring to the drawings, where FIG. 1 shows an exploded view of said syringe. Syringe 1 includes a hollow cylinder or barrel 2 which is to be infused with a supply of fluid that is to be injected through the tissue of the patient. A piston assembly, comprising a piston stem 4 and an elastomeric (e.g. rubber) gasket 6, is received within and slidable reciprocally through cylinder 2 so as to expulse the supply of fluid therefrom. The piston stem 4 includes a piston head 8 formed at one end to which the gasket 6 is attached to complete the piston assembly. Piston head 8 has an offset locking bore 10 formed therein for an important purpose that will be described in greater detail hereafter.

Coextensively formed at the distal aspect of syringe cylinder 2 is a needle hub 12. Integrally connected to and projecting proximally into cylinder 2 from needle hub 12 is a tapered locking and retraction probe 14. Locking and retraction probe 14 is, in the assembled, as-packaged configuration of FIG. 2, arranged in spaced, axial alignment with the entrance to locking bore 10. The needle hub 12 includes a space in which to receive and releasably retain a pair of rotatable, spring-like jaws 16 that are biased in a normally open configuration and adapted to be advanced axially and distally through said hub, in a manner that will be described when referring to FIG. 5. In the assembled, as-packaged configuration (of FIGS. 2 and 3), a sterile needle cannula 18 is coaxially aligned with and fixedly attached to the needle hub 12. Needle cannula 18 has a conventional design and includes a sharp distal tip that extends outwardly from hub 12 for penetrating the skin of a patient and a blunt proximal end to be received between the jaws 16 and bonded at the interior of hub 12. A removable needle sheath 20 is to be detachably connected to needle hub 12 so as to surround the distal tip of cannula 18 and thereby prevent an accidental needle stick and/or the loss of sterility.

FIGS. 2 and 3 of the drawings show the syringe 1 in the assembled, as-packaged configuration with the jaws 16 located within the needle hub 12 and the needle cannula 18 bonded to said hub and extending axially therefrom so as to administer an injection. More particularly, and as is best shown in FIG. 3, needle hub 12 includes and outer sleeve 22 that is integrally connected (i.e. molded) to a relatively thick shield 24 formed at the distal aspect of syringe cylinder 2. Needle hub 12 also includes a central core 26 that is coaxially aligned with and spaced inwardly of outer sleeve 22. The outer sleeve 22 and inner central core 26 of needle hub 12 are connected together at a relatively thin, breakaway sealing web 28.

The central core 26 of hub 12 has a hollow channel 30 extending longitudinally therethrough. The proximal end of needle cannula 18 is received within channel 30 to be bonded to central core 26. By way of example, an adhesive material (e.g. epoxy) 32 is used in accordance with well known bonding techniques to affix cannula 18 to needle hub 12 within the central core 26 thereof. An entry port 34 is formed between the channel 30 of central core 26 and the syringe cylinder 2 so as to complete a fluid path between said cylinder and the needle cannula 18, whereby fluid within the cylinder may be expulsed via said cannula. Integrally formed with and projecting proximally from the central core 26 into cylinder 2 is the locking and retraction probe 14. Probe 14 is provided with a slight (e.g. 2 degree) taper for an advantage that will soon be described.

As previously pointed out, the outer sleeve 22 and inner central core 26 of needle hub 12 are arranged in spaced, coaxial alignment with one another. Releasably retained within the space between outer sleeve 22 and central core 26 is the pair of spring-like jaws 16. The jaws 16 have a peripheral lip 36 projecting radially outward therefrom. Projecting radially inward from the outer sleeve 22 of hub 12 are axially spaced primary and secondary locking rings 37 and 38. In the as-packaged configuration of FIG. 3, the peripheral lip 36 of jaws 16 is seated against the primary locking ring 37 of outer sleeve 22 to prevent a premature distal displacement of said jaws relative to needle hub 12. In the as-packaged configuration, the jaws 16 are rotated towards one another against their normally open bias so as to clamp the central core 26 of hub 12 and provide axial support for the needle cannula 18 which is affixed therein. Thus, the jaws 16 and the adhesive bonding material 32 act as redundant locking means to reliably retain the cannula 18 at the axially extended position within the channel 30 of the central core 26.

Located within cylinder 2 and spaced proximally from the locking and retraction probe 14 of needle hub 12 is the elastomeric gasket 6. Gasket 6 has a hollow interior in which the piston head 8 is received, whereby to attach gasket 6 to the piston stem 4 to complete the piston assembly. Piston head 8 is connected to stem 4 by way of a relatively narrow neck 40 and a laterally extending flange 42 upon which the gasket 6 is seated. Piston stem 4 has an area 44 of reduced cross section located proximally of flange 42. The piston stem 4 may be fractured at the narrow area 44 in response to the application of a bending force thereto, whereby to break the piston assembly and thereby prevent access to and reuse of the needle cannula 18 at the conclusion of the injection process.

As earlier disclosed, an offset locking bore 10 is formed through the piston head 8. The locking bore 10 is offset (i.e. angled) by approximately 10 degrees relative to the longitudinal axis of syringe 1. Moreover, locking bore 10 is provided with a slight (e.g. 2 degree) taper to match the taper of locking and retraction probe 14. A locating concavity 46 is formed in gasket 6, such that probe 14. A locating concavity 46 and the entrance to locking bore 10 are all spaced from and axially aligned with one another in the as-packaged configuration, whereby the piston head 8 and locking bore 10 therein can be moved into mating engagement with probe 14 in a manner that will now be disclosed.

FIG. 4 of the drawings shows the safety syringe 1 in the post-injection configuration after the piston stem 4 has been moved distally through syringe cylinder 2 and gasket 6 has been driven through said cylinder to expulse the fluid contents thereof via needle cannula 18. As gasket 6 moves distally through cylinder 2 and into contact with the relatively thick shield 24 at the distal aspect of cylinder 2, the proximally projecting locking and retraction probe 14 of needle hub 12 penetrates the gasket 6 for receipt within the locking bore 10 of piston head 8. Inasmuch as the locking bore 10 is angled and tapered, as previously disclosed, the proximal tip of locking and retraction probe 14 is both deflected by and locked in said locking bore 10. That is, by virtue of the deflection of locking and retraction probe 14 within bore 10, the needle hub 12 and piston head 8 are fixedly connected to one another.

Figure 5:
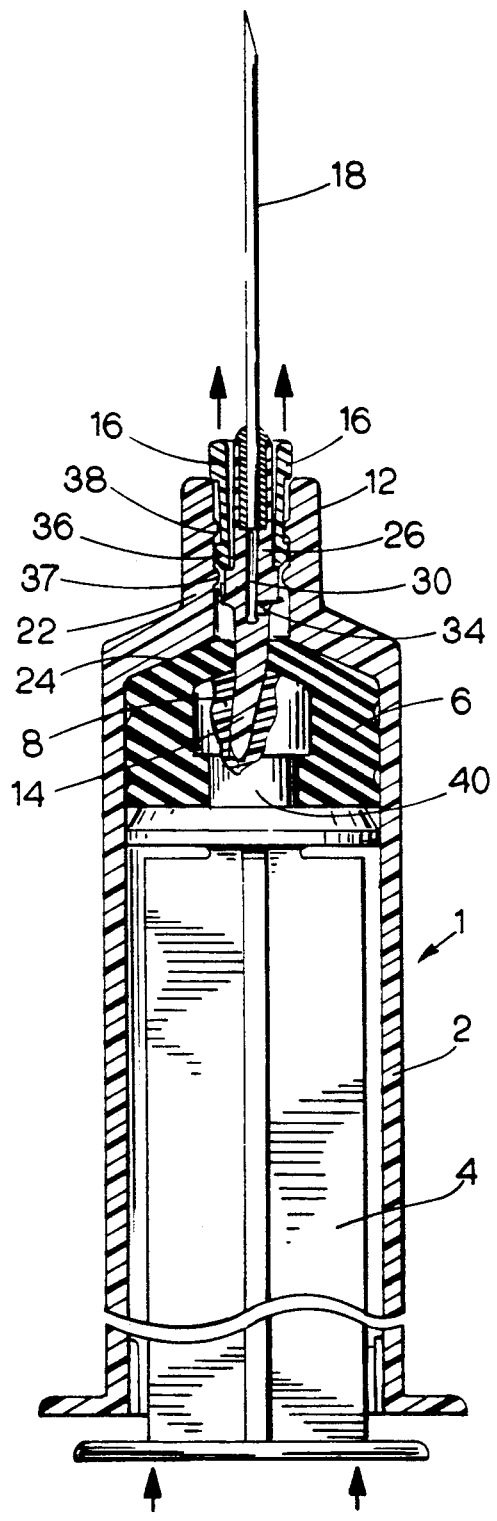

Referring now to FIG. 5 of the drawings, with syringe 1 still in the post-injection configuration and piston gasket 6 pushed against the thick shield 24 at the distal aspect of syringe cylinder 2, and axial and distal pushing force is applied to piston stem 4. Accordingly, the gasket 6 is compressed against shield 24, whereby to efficiently expulse any remaining fluid in cylinder 2 via cannula 18 and the fluid path including the entry port 34 and the longitudinal channel 30 through the central core 26 of needle hub 12. Moreover, the compression of gasket 6 causes the sealing pressure exerted by said gasket upon the piston head 8 and neck 40 to be enhanced, whereby the syringe 1 is adapted to reliably withstand high back pressure and thereby prevent the back flow or leakage of fluid into cylinder 2.

What is more, the breakaway web (designated 28 in FIG. 3) which connected together the outer sleeve 22 and inner central core 26 of needle hub 12 in the as-packaged configuration of syringe 1 is broken. More particularly, and inasmuch as the central core 26 of hub 12 is fixedly connected to the piston head 8 at the locking and retraction probe 14, a distal pushing force applied to piston stem 4 is transferred to said central core 26 by way of probe 14. Accordingly, the central core 26 is displaced axially and distally relative to the outer sleeve 22 of needle hub 12, such that a shear breaking force is generated to fracture web 28.

What is still more, the distal displacement of the central core 26 of needle hub 12 causes a corresponding distal relocation of the jaws 16 relative to outer sleeve 22. That is, the axial pushing force that is transferred from piston stem 4 to central core 26 by way of probe 14 is also transferred by way of said central core 26 to jaws 16, such that the peripheral lip 36 thereof is moved past the primary locking ring 37 of outer sleeve 22. Jaws 16 are advanced distally and outwardly of outer sleeve 22 until the peripheral lip 36 thereof is moved into contact with and seated against the secondary locking ring 37 of sleeve 22 (best shown in FIG. 6). In their distally advanced position relative to outer sleeve 22, the normally open, spring-like jaws 16 automatically rotate away from one another to remove the clamping force applied to the central core 26 of needle hub 12. Thus, cannula 18 is now released from the as-packaged, locked condition of FIG. 3.

Figure 6:
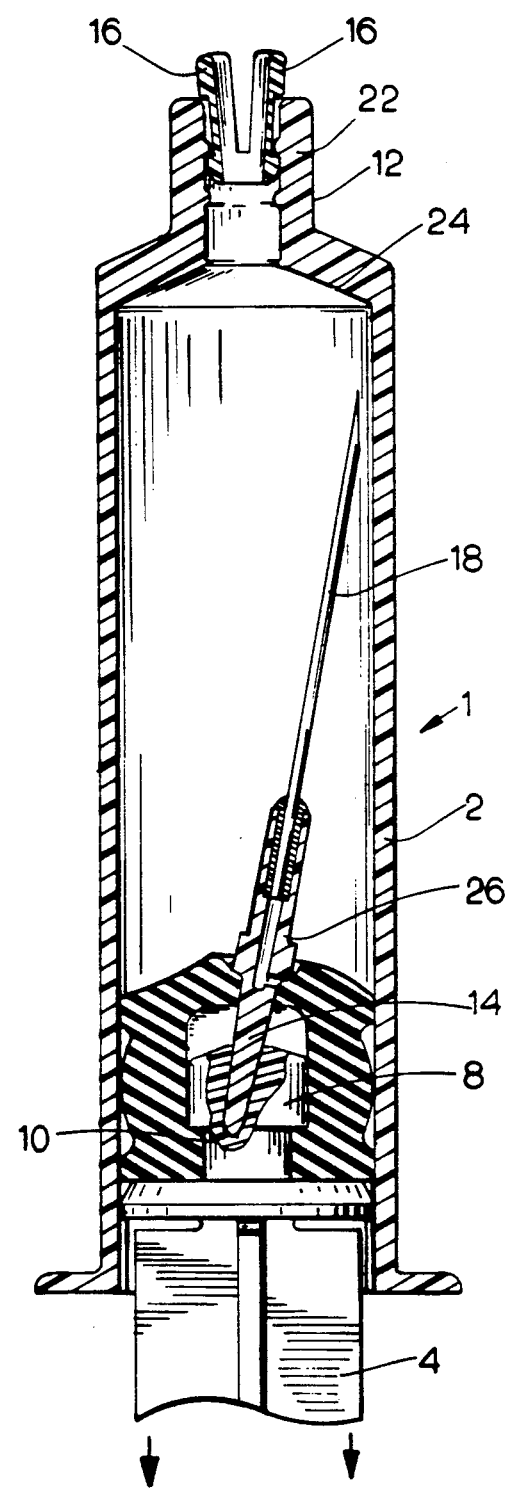

FIG. 6 of the drawings shows the needle cannula 18 retracted into the cylinder 2 of safety syringe 1 so as to prevent an accidental needle stick during the handling and/or disposal of said syringe to thereby prevent the spread of a contagious, and possibly life threatening, disease. That is to say, with the jaws 16 advanced distally and outwardly of the outer sleeve 22 of needle hub 12 to release cannula 18, a proximal pulling force is applied to piston stem 4. Inasmuch as the central core 26 of needle hub 12 is fixedly connected to piston stem 4 (by virtue of the receipt of locking and retraction probe 14 within the locking bore 10 of piston head 8), the proximal pulling force applied to stem 4 is transferred to needle cannula 18 by way of probe 14 and central core 26. Hence, the cannula 18 is withdrawn from the axially extended position (of FIG. 3), at which an injection was administered, to a retracted position, at which to be completely surrounded and safely shielded by the syringe cylinder 2. The deflective stresses generated by the connection of locking and retraction probe 14 at the offset locking bore 10 of piston head 8 causes the cannula 18 to be canted (in a direction towards the distal shield 24) within cylinder 2 so as to prevent an inadvertent return of the cannula to the axially extended position in the event that the piston stem 4 is pushed distally through cylinder 2.

Figure 7:
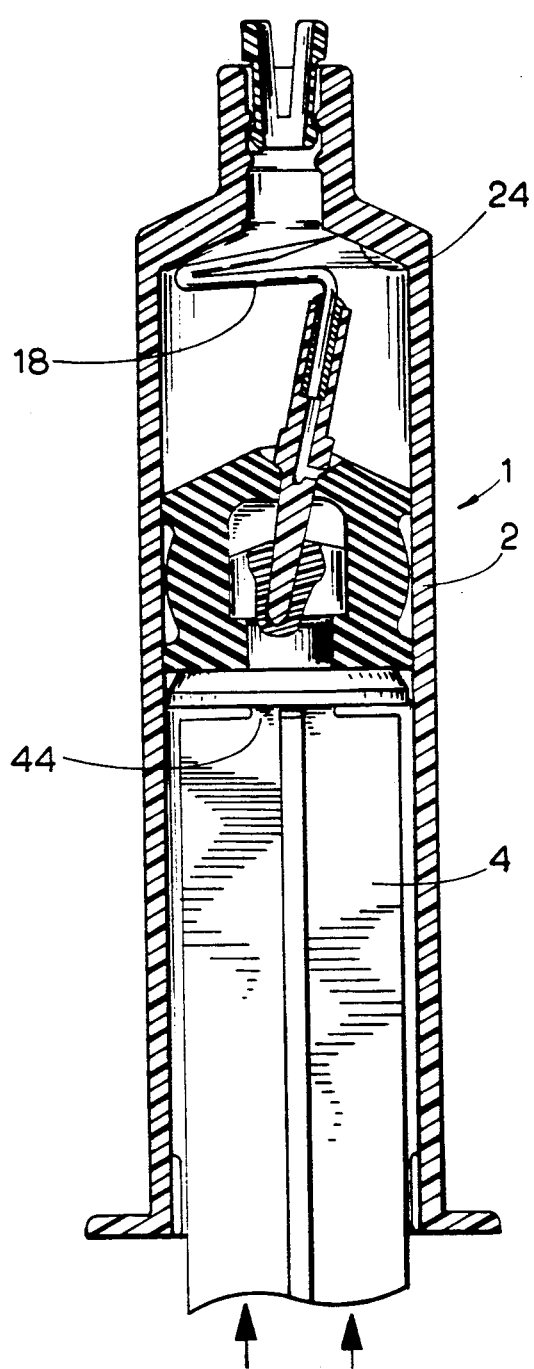

In FIG. 7 of the drawings, the needle cannula 18 of safety syringe 1 is axially collapsed and destroyed against the relatively thick shield 24 formed at the distal aspect of cylinder 2. More particularly, by once again pushing piston stem 4 distally through the cylinder 2, the cannula 18, because of its canted alignment, is moved into contact with shield 24. Therefore, the continued movement of stem 4 through cylinder 2 will cause said cannula 18 to collapse and be rendered non-usable. To facilitate the collapse and destruction of cannula 18, an additional, non-penetrable shielding surface (not shown) may be located at the interior of cylinder 2 below shield 24. Such as shielding surface is described in U.S. Pat. No. 4,804,370 issued Feb. 14, 1989 and assigned to the assignee of this patent application.

With the cannula 18 axially collapsed and destroyed, a bending force may be applied to piston stem 4 to break said stem 4 at the area 44 of reduced cross-section. The piston stem 4 is then discarded, rendering the cannula 18 non-reusable and inaccessible within the cylinder 2. Hence, a compact disposable package is available to permit a safe handling and/or disposal of syringe 1 without the threat of an accidental needle stick and the consequences resulting therefrom.

Figure 8:
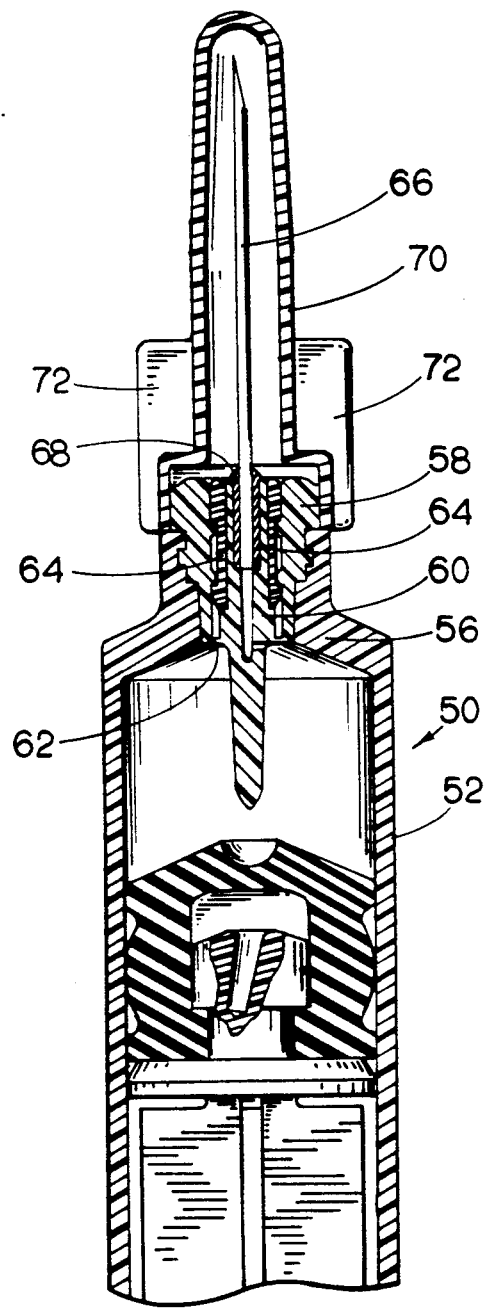
FIG. 8 is a partial cross-section of a disposable safety syringe according to an alternate embodiment of the present invention.

FIG. 8 of the drawings shows a cost-effective, disposable, safety syringe 50 that is formed in accordance with an alternate embodiment of the present invention. In the safety syringe 1 of FIGS. 1-7, the needle hub 12 is coextensively formed with and integrally connected to the distal aspect of the syringe cylinder 2. In the syringe 50 of FIG. 8, the needle hub 54 is screwed into the syringe cylinder 52 so that the syringe 50 and the needle cannula 66 carried by hub 54 can be packaged and transported separately from one another, whereby to permit different cannulas to be used with a common syringe cylinder 52. More particularly, the distal aspect of cylinder 52 is provided with a hollow, axially extending and screw threaded neck 56. Needle hub 54 comprises a coaxially arranged outer sleeve 58 and central core 60 that are connected together by a relatively thin, breakaway sealing web 62. A pair of jaws 64 is received between outer sleeve 58 and central core 60. The outer sleeve 58 of hub 54 is screw threaded and thereby adapted to be mated to the screw threaded neck 56 of cylinder 52.

To facilitate the attachment of needle hub 54 to neck 56, the needle cannula 66 (which is fixedly connected to the central core 60 of hub 54 by means of a bonding material 68, such as epoxy, or the like) is surrounded by a needle sheath 70 having a pair of torque applying ears 72 extending radially outwardly therefrom. Needle sheath 70 is detachably connected (i.e. snap fit) to the outer sleeve 58 of needle hub 54. Therefore, a rotational force applied to the ears 72 of sheath 70 is transferred to the outer sleeve 58 for rotating needle hub 54 into mating engagement with the screw threaded neck 56 of cylinder 52. With hub 54 attached to neck 56, the sheath 70 may be removed from cannula 66 and discarded so that an injection may be administered.

The remaining structure and the operation of the safety syringe 50 of FIG. 8 is identical to that previously described when referring to the syringe 1 of FIGS. 1-7. Therefore, for purposes of economy, the remaining structure and operation of syringe 50 will not be described again.

It should be apparent that the syringes 1 and 50 of the present invention can be manufactured in a cost effective manner while providing the needle retracting, canting and destroying advantages disclosed herein. That is to say, the needle cannula associated with syringes 1 and 50 is of conventional design and has a single sharpened end (as opposed to a pair of sharpened ends). Moreover, the cannula can be manufactured without an integral fluid port, since fluid is supplied from the syringe cylinder to said cannula via a path including the channel 30 and entry port 34 (of FIG. 3) formed through the needle hub. What is more, the cannula is fixedly connected to the needle hub by means of bonding procedures that are common to the syringe art. Accordingly, a disposable safety syringe having the safety features of the disclosed invention can be manufactured at approximately the same cost as a conventional syringe without said features and advantages.

It will be apparent that while a preferred embodiment of the invention has been shown and described, various modifications and changes may be made without departing from the true spirit and scope of the invention.

Having thus set forth a preferred embodiment of the invention, what is claimed is:

1. A syringe comprising:
   a cylinder having proximal and distal ends and receiving a supply of fluid at the interior thereof;
   a hypodermic needle cannula communicating fluidically with the cylinder and projecting outwardly from the distal end thereof for penetrating a targeted tissue area;
   a needle hub having an outer sleeve attached to the distal end of said cylinder and an inner core surrounding and attached to the needle cannula and received within and spaced from said outer sleeve, said outer sleeve and inner core connected together by means of a breakaway web;
   a piston assembly movable reciprocally through said cylinder and having force applying means for moving the inner core of said needle hub relative to said outer sleeve and breaking the breakaway web connected therebetween to disconnect said core from said sleeve and detach said needle cannula from the distal end of said cylinder; and
   clamping means received in the space between the outer sleeve and the inner core of said needle hub so as to apply a clamping force to said inner core to prevent the removal of said needle cannula therefrom, said clamping means being moved with said inner core relative to said outer sleeve and outwardly from the space between said core and said sleeve at which the clamping force applied to said inner core is removed.

2. The syringe recited in claim 1, wherein the outer sleeve of said needle hub is integrally and fixedly connected to the distal end of said cylinder.

3. The syringe recited in claim 1, wherein the outer sleeve of said needle hub is detachably connected to the distal end of said cylinder.

4. The syringe recited in claim 1, wherein the inner core of said needle hub has a longitudinally extending channel formed therein in which to receive the needle cannula and a hollow fluid entry port extending between said channel and the cylinder to establish a fluid path between said cylinder and said cannula.

5. The syringe recited in claim 1, wherein said clamping means includes a set of normally open jaws that are closed against the inner core of said needle hub when said jaws are located between the outer sleeve and inner core of said hub.

6. The syringe as recited in claim 1, further comprising force transferring means projecting proximally from the inner core of said needle hub into said cylinder, the force applying means of said piston assembly engaging the force transferring means of said inner core when said piston assembly is moved through said cylinder for moving said inner core relative to said outer sleeve and breaking the web between said sleeve and said core.

7. The syringe recited in claim 1, further comprising means for retracting the needle cannula into the cylinder after the inner core of said needle hub has been moved relative to said outer sleeve and said breakaway web therebetween has been broken.

8. The syringe recited in claim 7, wherein said means for retracting the needle cannula includes a locking and retraction probe projecting proximally from the inner core of said needle hub into the cylinder and a locking bore formed in said piston assembly, said locking and retraction probe being received within said locking bore for connected said inner core to said piston assembly, such that a proximal movement of said piston assembly through the cylinder causes a corresponding retraction of said cannula into said cylinder.

9. The syringe of claim 8, wherein the locking bore of said piston assembly is angled relative to the longitudinal axis of said cylinder, such that said locking and retraction probe is deflected by and locked within said bore.

10. The syringe recited in claim 9, wherein the needle cannula is canted when retracted into the cylinder, said syringe further comprising a relatively thick shield formed at the distal aspect of said cylinder for collapsing and destroying said cannula when said piston assembly is moved distally through said cylinder and said canted cannula is moved into contact with said shield.

11. The syringe recited in claim 8, wherein said piston assembly includes a piston stem, a piston head attached to said stem, and a hollow gasket surrounding said head and movable through the cylinder to expulse the fluid contents thereof by way of the cannula, said locking bore being formed in the piston head of said piston assembly and located at the interior of said gasket.

12. A syringe comprising:
    a cylinder having proximal and distal ends and receiving a supply of fluid at the interior thereof;
    a hypodermic needle cannula communicating fluidically with the cylinder and projecting outwardly from the distal end thereof for penetrating a targeted tissue area;
    needle hub means attached to and supporting the needle cannula, said needle hub means connected to the distal end of said cylinder by a breakaway web;

a piston assembly movable reciprocally through said cylinder;

a locking and retraction probe projecting proximately from said needle hub means into said cylinder; and a locking bore formed in said piston assembly, such that a distal movement of said piston assembly through said cylinder causes said locking and retraction probe to be received within said locking bore to connect said piston assembly to said needle hub means and said needle hub means to be displaced relative to the distal end of said cylinder to break the breakaway web therebetween, and a proximal movement of said piston assembly through the cylinder causes a retraction of said needle hub means and the cannula attached thereto into the interior of said cylinder, said locking bore being angled relative to the longitudinal axis of the cylinder, such that said locking and retraction probe is deflected by and locked within said bore and said needle cannula is canted when retracted into the cylinder by said piston assembly.

13. The syringe recited in claim 12, wherein said needle hub means has a longitudinally extending channel formed therein in which to receive the needle cannula and a hollow fluid entry port extending between said channel and said cylinder to establish a fluid path between said cylinder and said cannula.

14. The syringe recited in claim 12, further comprising a relatively thick shield formed at the distal aspect of said cylinder for collapsing and destroying said cannula when said piston assembly is moved distally through said cylinder and said canted cannula is moved into contact with said shield.

15. The syringe recited in claim 12, further comprising clamping means located between said needle hub means and the distal end of said cylinder to apply a clamping force to said hub means to prevent the detachment of said cannula from said hub means, said clamping means being displaced with said hub means relative to the distal end of said cylinder to remove the clamping force applied to said hub means.

16. The syringe recited in claim 15, wherein said clamping means includes a set of normally open jaws that are closed against said needle hub means when said jaws are located between said hub means and the distal end of said cylinder.

17. The syringe recited in claim 15, further comprising an inwardly extending locking ring formed around the periphery of the distal end of said cylinder for engaging said clamping means and preventing an unintentional displacement of said clamping means relative to said distal end.

18. A syringe comprising:

a cylinder having proximal and distal ends and receiving a supply of fluid at the interior thereof;

a hypodermic needle cannula communicating fluidically with the cylinder and projecting outwardly from the distal end thereof for penetrating a targeted tissue area;

a needle hub received within and retained at the distal end of the cylinder and connected to said needle cannula, said needle hub having locking and retracting means projecting proximally therefrom into the cylinder; and a piston assembly movable reciprocally through the cylinder and having a locking bore formed therein, said piston assembly moving distally through the cylinder to expulse the fluid thereof through said cannula and to move the locking bore of said piston assembly into receipt of the locking and retracting means of said needle hub such that said piston assembly is connected to said needle hub, and said piston assembly moving proximally through the cylinder to retract said needle hub and the cannula connected thereto into the interior of said cylinder, said locking bore being angled relative to the longitudinal axis of the cylinder, so that said locking and retracting means is deflected by and locked within said bore and said needle cannula is canted when retracted into said cylinder by said piston assembly.

* * * * *